(12) United States Patent
Narveson

(10) Patent No.: US 8,628,550 B2
(45) Date of Patent: Jan. 14, 2014

(54) ROTATIONAL ATHERECTOMY SEGMENTED ABRADING HEAD AND METHOD TO IMPROVE ABRADING EFFICIENCY

(75) Inventor: Christopher M. Narveson, Minneapolis, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 622 days.

(21) Appl. No.: 12/388,703

(22) Filed: Feb. 19, 2009

(65) Prior Publication Data
US 2010/0211088 A1    Aug. 19, 2010

(51) Int. Cl.
*A61B 17/22* (2006.01)
(52) U.S. Cl.
USPC .......................................... 606/159
(58) Field of Classification Search
USPC ............ 606/159, 167, 170, 171, 180; 604/22, 604/104
See application file for complete search history.

(56) References Cited

U.S. PATENT DOCUMENTS

| | | | |
|---|---|---|---|
| 5,403,334 A | 4/1995 | Evans et al. | |
| 5,501,694 A * | 3/1996 | Ressemann et al. | 606/159 |
| 5,540,707 A * | 7/1996 | Ressemann et al. | 606/159 |
| 5,584,843 A * | 12/1996 | Wulfman et al. | 606/159 |
| 5,681,336 A * | 10/1997 | Clement et al. | 606/159 |
| 5,925,055 A | 7/1999 | Adrian et al. | |
| 6,019,772 A | 2/2000 | Shefaram et al. | |
| 6,183,432 B1 | 2/2001 | Milo | |
| 6,235,042 B1 | 5/2001 | Katzman | |
| 6,258,052 B1 | 7/2001 | Milo | |
| 6,494,890 B1 * | 12/2002 | Shturman et al. | 606/159 |
| 6,579,299 B2 | 6/2003 | McGuckin, Jr. et al. | |
| 6,800,083 B2 | 10/2004 | Hiblar et al. | |
| RE40,305 E | 5/2008 | Richter | |
| 7,381,198 B2 | 6/2008 | Noriega et al. | |
| 2002/0077638 A1 * | 6/2002 | Kadavy et al. | 606/159 |
| 2003/0125756 A1 * | 7/2003 | Shturman et al. | 606/159 |
| 2005/0149083 A1 * | 7/2005 | Prudnikov et al. | 606/159 |
| 2006/0142793 A9 * | 6/2006 | Prudnikov et al. | 606/159 |
| 2008/0306498 A1 * | 12/2008 | Thatcher et al. | 606/159 |

OTHER PUBLICATIONS http://www.thefreedictionary.com/segment; definition of the word "segment".*

* cited by examiner

*Primary Examiner* — Ryan Severson
*Assistant Examiner* — David Eastwood
(74) *Attorney, Agent, or Firm* — Winthrop & Weinstine, P.A.

(57) ABSTRACT

The invention provides a rotational atherectomy system, device and method having, in various embodiments, a flexible, elongated, rotatable drive shaft comprising an eccentric abrading head comprising at least one eccentric abrading cylindrical segments attached to the drive shaft and in spaced proximity with proximal and a distal conical segments. Each individual abrading segment, comprises a first tissue removing surface, typically an abrasive coating on the outer surface, that is designed to abrade calcified, hard tissue and abrasive coating on the leading and trailing surfaces designed to abrade non-calcified, soft tissue. Each abrading segment, as well as the abrading head comprising the collective segments, has a center of mass spaced radially from the rotational axis of the drive shaft, facilitating the ability of the device to open the stenotic lesion to a diameter larger than the outer diameter of the enlarged abrading head when operated at high speeds.

14 Claims, 10 Drawing Sheets

ROTATIONAL ATHERECTOMY SEGMENTED ABRADING HEAD AND METHOD TO IMPROVE ABRADING EFFICIENCY

BACKGROUND OF THE INVENTION

1. Field of the Invention

The invention relates to systems, devices and methods for removing tissue from body passageways, such as removal of atherosclerotic plaque from arteries, utilizing a high-speed rotational atherectomy device.

2. Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patentcy of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove stenotic material. In one type of device, such as that shown in U.S. Pat. No. 4,990,134 (Auth), a burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438 (Shturman) discloses another atherectomy device having a drive shaft with a section of the drive shaft having an enlarged diameter, at least a segment of this enlarged surface being covered with an abrasive material to define an abrasive segment of the drive shaft. When rotated at high speeds, the abrasive segment is capable of removing stenotic tissue from an artery. Though this atherectomy device possesses certain advantages over the Auth device due to its flexibility, it also is capable only of opening an artery to a diameter about equal to the diameter of the enlarged abrading surface of the drive shaft since the device is not eccentric in nature.

U.S. Pat. No. 6,494,890 (Shturman) discloses an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. Since the enlarged eccentric section comprises drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. In addition, some stenotic tissue may block the passageway so completely that the Shturman device cannot be placed therethrough. Since Shturman requires that the enlarged eccentric section of the drive shaft be placed within the stenotic tissue to achieve abrasion, it will be less effective in cases where the enlarged eccentric section is prevented from moving into the stenosis. The disclosure of U.S. Pat. No. 6,494,890 is hereby incorporated by reference in its entirety.

U.S. Pat. No. 5,681,336 (Clement) provides an eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., 20,000-200,000 rpm. Essentially, the center of mass offset from the rotational axis of the drive shaft would result in development of significant centrifugal force, exerting too much pressure on the wall of the artery and creating too much heat and excessively large particles.

In general, current tissue-removing elements are of a one-piece solid design which is inflexible and, as a result, may be difficult to advance/retract through tortuous vasculature. In addition, known designs typically comprise continuous, unbroken, abrasive surfaces in e.g., either a symmetrical or asymmetrical elliptical or spherical configuration. It is known that a hydraulic wedge forms in some cases between the current tissue-removing element design and the arterial wall and plaque, reducing the contact between the abrasive and the plaque and, as a result, reducing the efficacy of the procedure. Moreover, the relatively smooth abrasive face of current designs does not maximize abrading and/or cutting efficacy. Finally, the known relatively smooth tissue-removing element designs result in atherectomy procedures of unpredictable length when working with soft plaque and/or non-calcified lesions and/or diffuse lesions.

Accordingly, there exists a need for an atherectomy device having a tissue-removing element with individual eccentric abrading segments of selectable and customizable number and comprising additional cutting edges and sanding surfaces as well as providing a mechanism for breaking the hydraulic wedge that exists between the abrasive and the arterial wall and plaque. In addition, a need exists for a tissue-removing element that can be customized to allow effective abrasion of both hard and soft, non-calcified plaque, thereby increasing the predictability of procedure outcome and length when working with such blockages comprising hard, soft, non-calcified and/or diffuse stenotic tissue. Further, All current designs comprise a fixed amount of mass and, as a result, a fixed rotational diameter. Thus, there exists a need for an abrading head that can be customized in terms of the amount of eccentric mass present. This allows, in turn, customization of the eccentric abrading head's rotational diameter.

BRIEF SUMMARY OF THE INVENTION

The invention provides a rotational atherectomy system, device and method having, in various embodiments, a flexible, elongated, rotatable drive shaft comprising an eccentric abrading head comprising at least one eccentric abrading cylindrical segment attached to the drive shaft and in spaced proximity with proximal and distal abrading segments. Each individual abrading segment, comprises a first tissue removing surface, typically an abrasive coating on the outer surface, that is designed to abrade calcified, hard tissue and abrasive coating on the leading and trailing surfaces designed to abrade non-calcified, soft tissue. Each abrading segment, as well as the abrading head comprising the collective segments, has a center of mass spaced radially from the rotational axis of the drive shaft, facilitating the ability of the device to open the stenotic lesion to a diameter larger than the outer diameter of the enlarged abrading head when operated at high speeds.

An object of the invention is to provide a high-speed rotational atherectomy device comprising an eccentric abrading head comprising at least one eccentric abrading cylindrical segment, preferably disc-shaped, attached to the drive shaft and proximal and distal conical segments, the at least one eccentric abrading cylindrical segment in spaced proximity with both the proximal and distal conical segments.

Another object of the invention is to provide a high-speed rotational atherectomy device comprising an eccentric abrading head comprising at least one eccentric abrading cylindrical segment, preferably disc-shaped, attached to the drive shaft and proximal and distal segments, the at least one eccentric abrading cylindrical segment in spaced proximity with both the proximal and distal segments and wherein the proximal and distal segments comprise a conical section and a cylindrical section.

Another object of the invention is to provide a high-speed rotational atherectomy device comprising an eccentric abrading head comprising at least one eccentric abrading cylindrical segment attached to the drive shaft and proximal and distal segments, the at least one eccentric abrading cylindrical segment in spaced proximity with both the proximal and distal segments, and an abrasive coating on the outer surface and on the leading and trailing surfaces of the at least one cylindrical segment, the abrasive coatings varying in grit size to optimize removal of calcified and non-calcified and/or soft stenotic tissue.

Another object of the invention is to provide a high-speed rotational atherectomy device comprising an eccentric abrading head comprising at least one eccentric abrading cylindrical segment attached to the drive shaft and proximal and distal segments, the at least one eccentric abrading cylindrical segment in spaced proximity with both the proximal and distal segments and further comprising a center of mass that is offset from the rotational axis of the atherectomy device's drive shaft.

Another object of the invention is to provide a high-speed rotational atherectomy device comprising an eccentric abrading head comprising at least one eccentric abrading cylindrical segment attached to the drive shaft and proximal and distal segments, the at least one eccentric abrading cylindrical segment in spaced proximity with both the proximal and distal segments and further comprising a customizable eccentricity for the abrading head during high-speed rotation by adding or subtracting additional eccentric abrading cylindrical segments from the abrading head, thus customizing the amount of mass comprising the abrading head and manipulating the center off mass offset from the rotational axis of the drive shaft.

Another object of the invention is to provide a high-speed rotational atherectomy device comprising an eccentric abrading head comprising at least one eccentric abrading cylindrical segment attached to the drive shaft and proximal and distal segments, the at least one eccentric abrading cylindrical segment in spaced proximity with both the proximal and distal conical segments and further comprising a center of mass that is offset from the rotational axis of the atherectomy device's drive shaft, wherein the proximal spacing of the at least one eccentric abrading cylindrical segment provides for flexibility of the abrading head during movement through tortuous vasculature.

Another object of the invention is to provide a high-speed rotational atherectomy device having at least one eccentric abrading cylindrical segment attached to the drive shaft and proximal and distal segments, the at least one eccentric abrading cylindrical segment in spaced proximity with both the proximal and distal segments and comprising complete gaps therebetween, the gaps improving efficacy in abrading non-calcified and/or soft stenotic tissue.

Another object of the invention is to provide a high-speed rotational atherectomy device having at least one eccentric abrading head comprising at least one eccentric abrading cylindrical segment attached to the drive shaft and proximal and distal segments, the at least one eccentric abrading cylindrical segment in spaced proximity with both the proximal and distal conical segments, the gap between adjacent cylindrical segments and/or cylindrical segment and the proximal and distal segments facilitating breaking the hydraulic wedge between the tissue removing surface and the stenotic tissue.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

Figure 1:
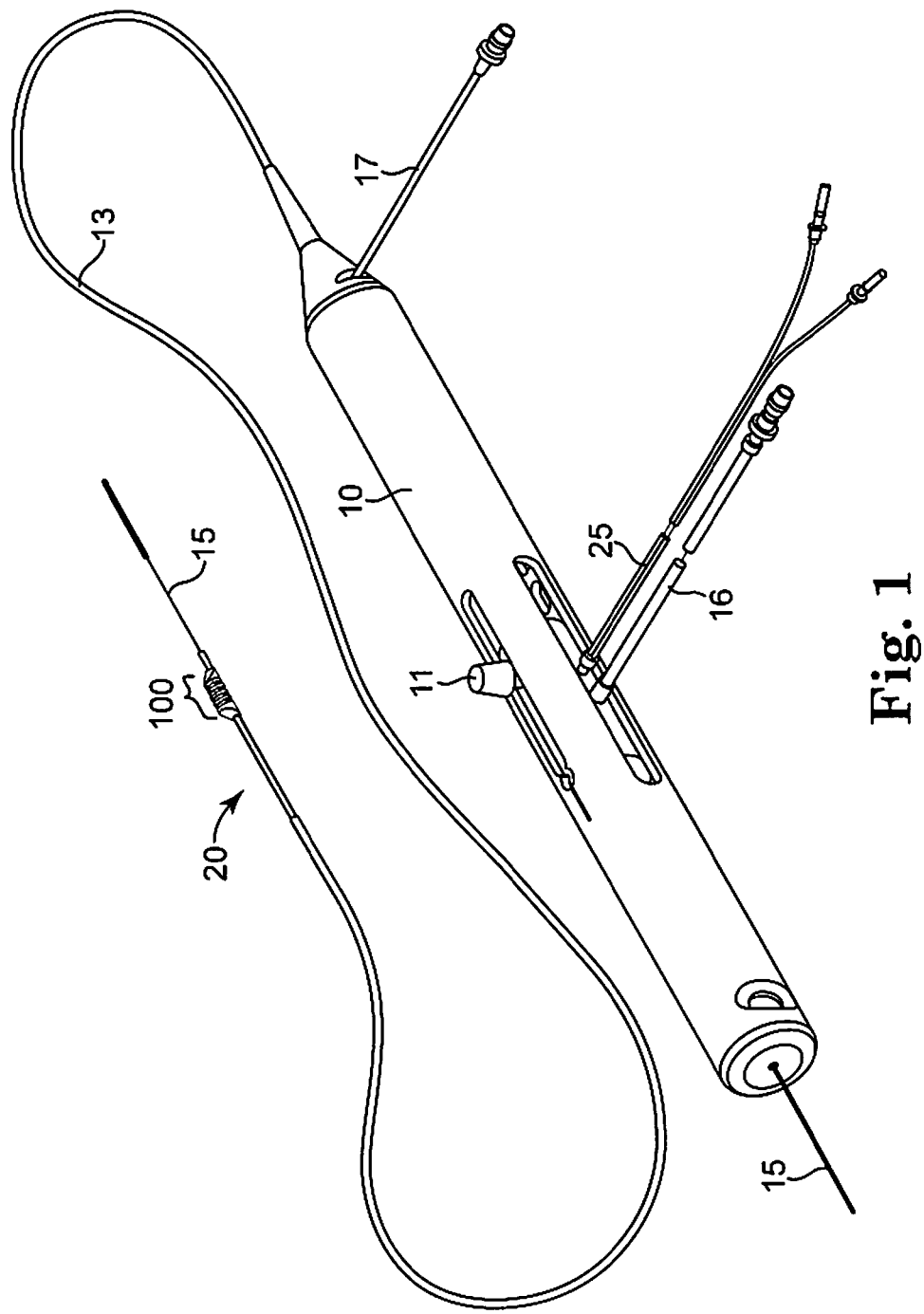
FIG. 1 is a perspective view of one embodiment of a non-flexible eccentric abrading head of a rotational atherectomy device of the invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

FIG. 1 illustrates one embodiment of a rotational atherectomy device according to the present invention. The device includes a handle portion 10, an elongated, flexible drive shaft 20 having an eccentric abrading head 100. As will be discussed herein, the abrading head 100 comprising a proximal and distal segment with an intermediate section comprising at least one eccentric cylindrical segment therebetween. An elongated catheter 13 extending distally from the handle portion 10. The drive shaft 20 is constructed from helically coiled wire as is known in the art and the abrading head 28 is fixedly attached thereto. The catheter 13 has a lumen in which most of the length of the drive shaft 20 is disposed, except for the enlarged abrading head 28 and a short section distal to the enlarged abrading head 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20 (details regarding such handles and associated instrumentation are well know in the industry, and are described, e.g., in U.S. Pat. No. 5,314,407, issued to Auth). The handle 10 also desirably includes a control knob 11 for advancing and retracting the turbine and drive shaft 20 with respect to the catheter 13 and the body of the handle.

Figure 2:
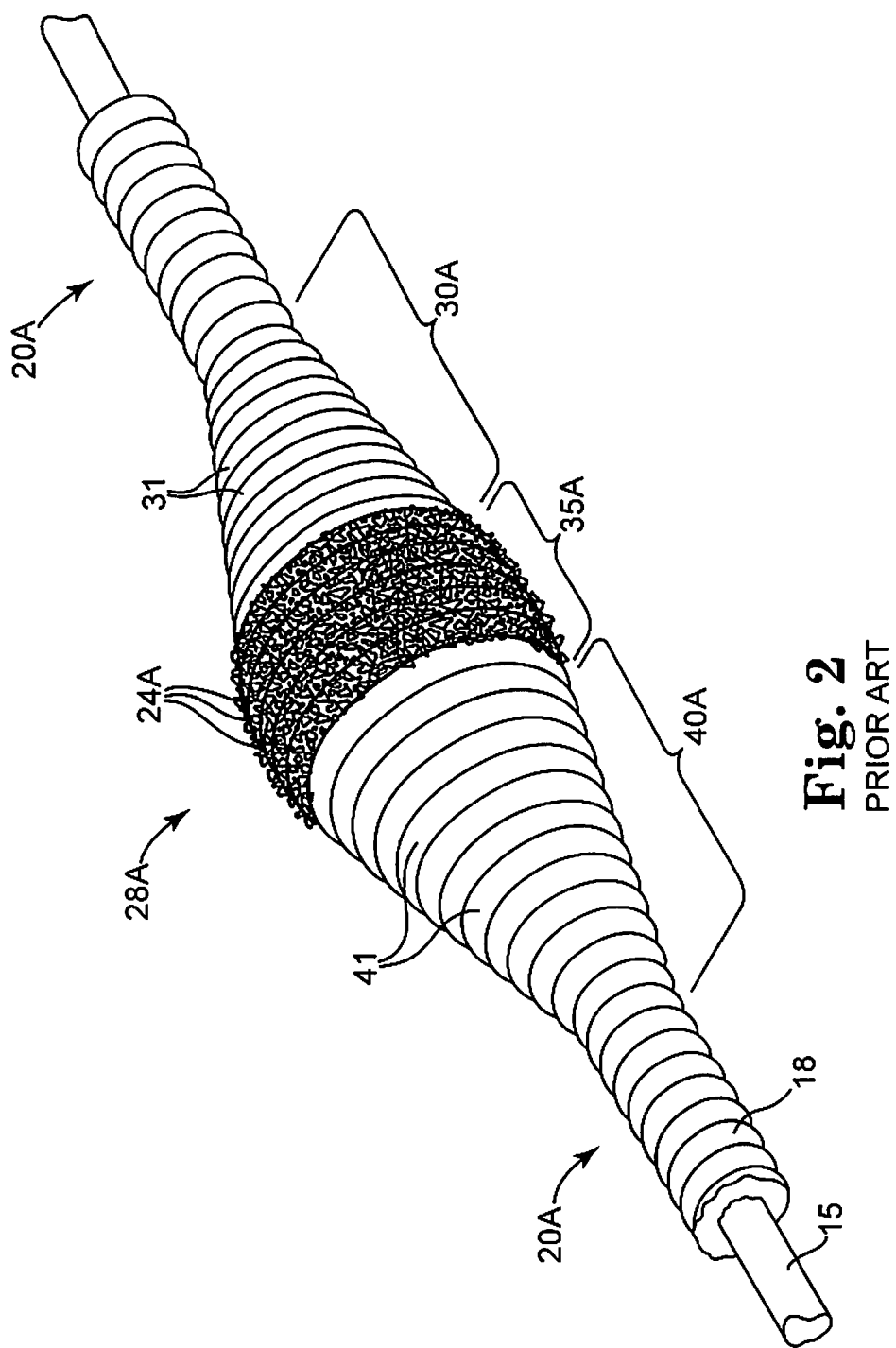
FIG. 2 is perspective, broken-away view of a prior art abrading head formed from wire turns of a rotatable drive shaft.
Figure 3:
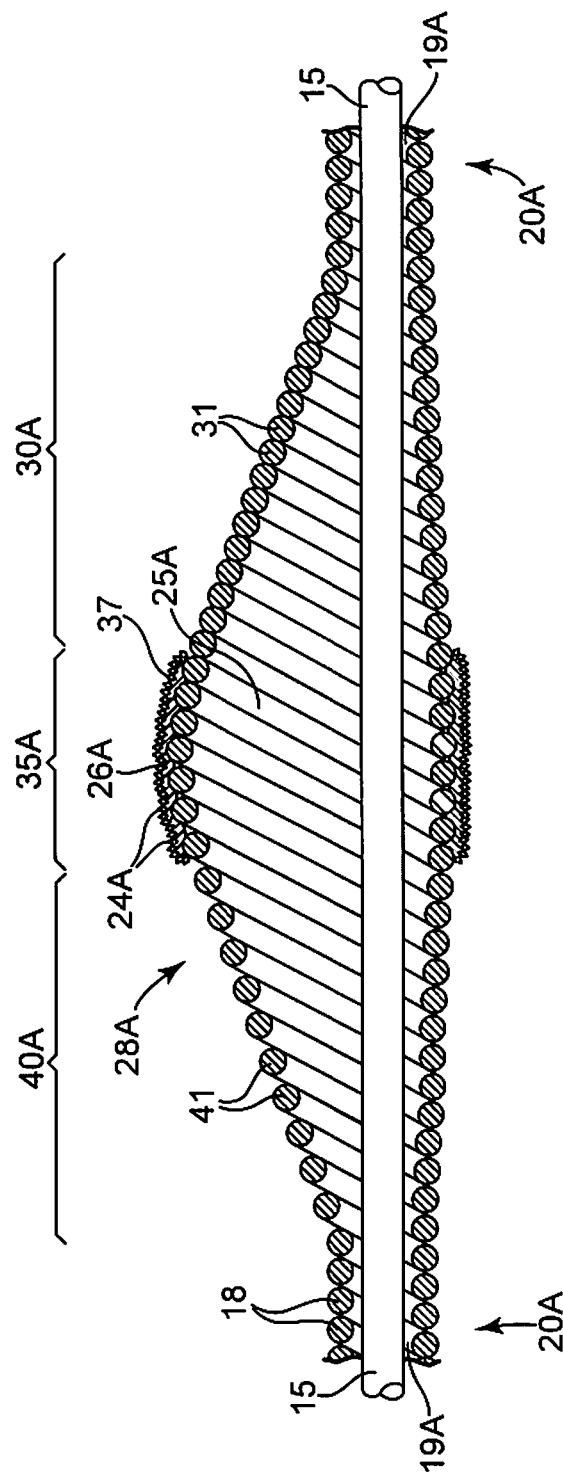
FIG. 3 is a broken-away, longitudinal cross-sectional view of a prior art eccentric abrading head formed from the wire turns of a rotatable drive shaft.

FIGS. 2 and 3 illustrate details of a prior art abrading head comprising an eccentric enlarged diameter abrading section 28A of a drive shaft 20A. The drive shaft 20A comprises one or more helically wound wires 18 which define a guide wire lumen 19A and a hollow cavity 25A within the enlarged abrading section 28A. Except for the guide wire 15 traversing the hollow cavity 25A, the hollow cavity 25A is substantially empty. The eccentric enlarged diameter abrading section 28A includes, relative to the location of the stenosis, proximal 30A, intermediate 35A and distal 40A portions. Wire turns 31 of the proximal portion 30A of the eccentric enlarged diameter section 28A preferably have diameters that progressively increase distally at a generally constant rate, thereby forming generally the shape of a cone. Wire turns 41 of the distal portion 40A preferably have diameters that progressively decrease distally at a generally constant rate, thereby forming generally the shape of a cone. Wire turns 36 of the intermediate portion 35A are provided with gradually changing diameters to provide a generally convex outer surface which is shaped to provide a smooth transition between the proximal and distal conical portions of the enlarged eccentric diameter section 28A of the drive shaft 20A.

Continuing with the prior art device, at least part of the eccentric enlarged diameter abrading section of the drive shaft 28A (preferably the intermediate portion 35A) comprises an external surface capable of removing tissue. A tissue removing surface 37 comprising a coating of an abrasive material 24A to define a tissue removing segment of the drive shaft 20A is shown attached directly to the wire turns of the drive shaft 20A by a suitable binder 26A.

Figure 4:
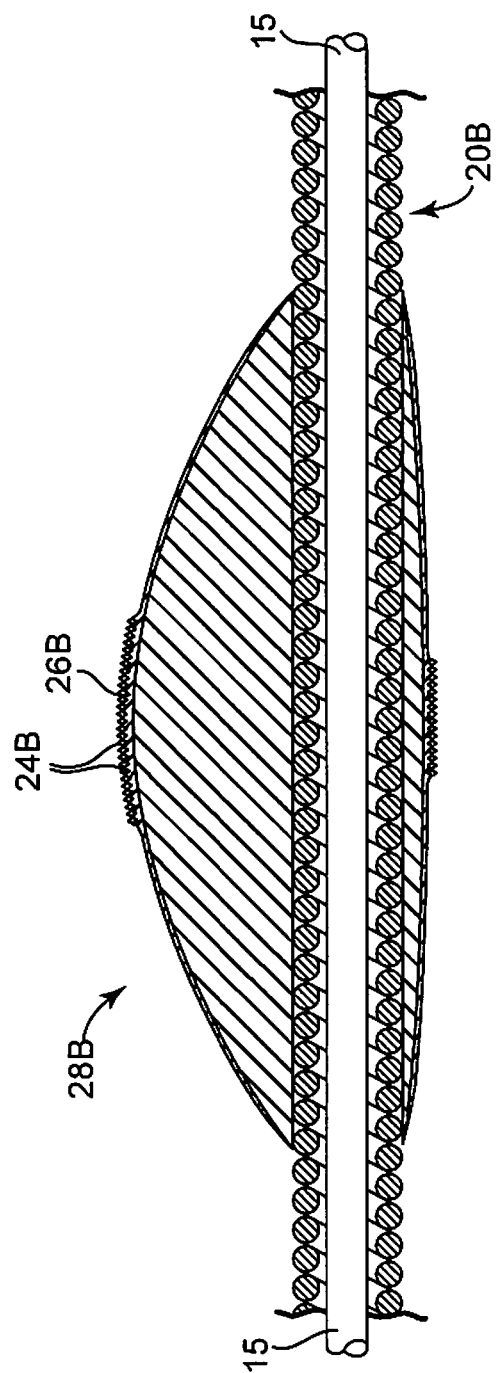
FIG. 4 is a broken away, longitudinal cross-sectional view of a prior art solid eccentric burr.

FIG. 4 illustrates another prior art rotational atherectomy device which, in contrast with the substantially hollow device of FIGS. 2 and 3, employs a solid asymmetrical abrasive burr 28B attached to a flexible drive shaft 20B, rotated over a guide wire 15 such as provided by U.S. Pat. No. 5,681,336 to Clement. The eccentric tissue removing burr 28B has a coating of abrasive particles 24B secured to a portion of its outer surface by a suitable binding material 26B. This construction has limited utility, however because, as Clement explains at Col. 3, lines 53-55, the asymmetrical burr 28B must be rotated at "lower speeds than are used with high speed ablation devices, to compensate for heat or imbalance." That is, given both the size and mass of the solid burr-type construction, it is infeasible to rotate such a burr at the high speeds used during atherectomy procedures, i.e., 20,000-200,000 rpm. Further, the abrasive section of this prior art device is relatively smooth, i.e., grooves are not present. As a result, this prior art device will be less than efficient when dealing with non-calcified and/or soft stenoses.

Figure 5:
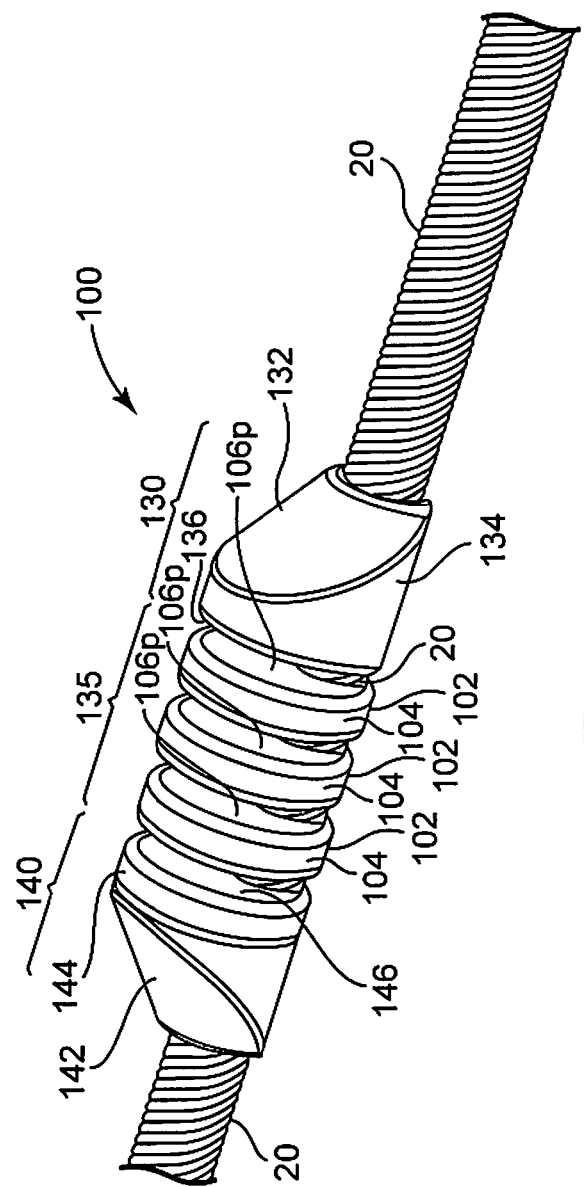
FIG. 5 is a perspective view of one embodiment of an eccentric abrading head of the present invention.
Figure 6:
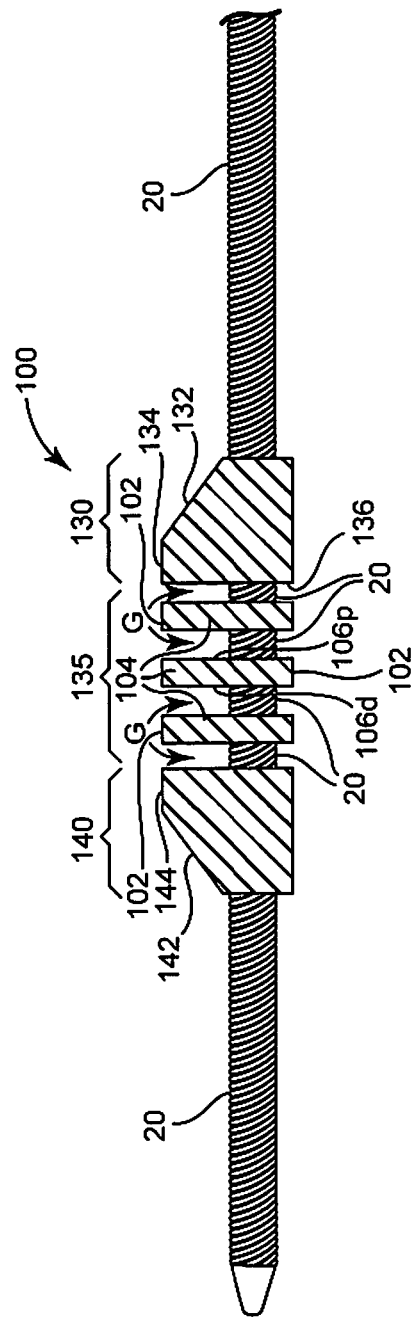
FIG. 6 is a side view of one embodiment of an abrading head of the present invention.

Turning now to FIGS. 5 and 6, one embodiment of the present invention is illustrated. The eccentric abrading head 100 comprises three sections: a proximal segment 130, a cylindrical-shaped intermediate section 135 and a distal segment 140, the intermediate section 135 located between the proximal and distal segments 130, 140 and spaced from the proximal and distal segments 130, 140.

The proximal segment 130 comprises a proximal outer surface and may further comprise a proximal conical section 132 and a proximal cylindrical section 134 and is mounted on the drive shaft 20. The intermediate section 135 comprises at least one eccentric abrading cylindrical segment 102 mounted on the drive shaft 20 at a point adjacent and distal to the proximal segment 130 and wherein the at least one eccentric abrading cylindrical segment 102 is spaced from the cylindrical section 134 of the proximal segment 130. In the embodiment illustrated, three eccentric abrading cylindrical segments 102 are provided. Each such eccentric abrading cylindrical segment 102 is spaced from the adjacent cylindrical segment 102. The distal segment 140 comprises a distal conical section 142 and a distal cylindrical section 140 and is mounted on the drive shaft 20 at a point adjacent and distal to the intermediate section 135. The proximal segment 130 and the distal segment 140 are mounted so that they are spaced from the adjacent cylindrical segment 102.

Proximal segment 130 further comprises a proximal inner surface 136, proximal inner surface 136 facing the interior of the eccentric abrading head 100 and specifically facing the adjacent eccentric cylindrical segment 102. Similarly, distal segment 140 further comprises a distal inner surface 146, wherein distal inner surface 146 faces the interior of the eccentric abrading head 100 and specifically faces the adjacent eccentric cylindrical segment 102 and in an opposing direction to that of proximal inner surface 136. As illustrated in the figures, proximal inner surface 136 and distal inner surface 146 are generally oriented in opposing directions with respect to each other.

Those skilled in the art will recognize that the proximal and/or distal segments 130, 140 may comprise, as described above, a conical section and a cylindrical section and/or segments 130, 140 may be of conical profile or of cylindrical profile.

Further, each of the at least one eccentric abrading cylindrical segments 102 comprise an outer surface 104 and proximal inner surface 106$p$ and distal inner surface 106$d$, the inner surfaces 106$p$ and 106$d$ located on opposite interior surfaces of each cylindrical segment. The outer surface 104 and/or proximal and distal inner surfaces 106$p$, 106$d$ may comprise an abrasive thereon. As is well known in the art, an abrasive coating 26, as illustrated in part in FIGS. 8-10, may be applied. It is contemplated that the abrasive grit size may be different on the outer surface 104 than applied on the proximal and distal inner surfaces 106$p$, 106$d$. The outer surface 104 may comprise an abrasive grit size that is optimized for removal of hard stenotic tissue, while the proximal and/or distal inner surfaces 106$p$, 106$d$ may comprise abrasive grit that is optimized for removal of soft, non-calcified and/or diffuse stenotic tissue.

As a result of the spaced mounting of the at least one cylindrical segment 102 and the proximal and distal segments 130, 140, flexibility gaps G are present between the proximal inner surface 146 and the adjacent cylindrical segment's opposing inner surface 106$p$ as well as between the distal outer surface 136 and the adjacent cylindrical segment's opposing distal inner surface 106$d$. Thus, in the simplest case involving a single cylindrical segment 102, a total of two flexibility gaps G will be present. In the case involving two cylindrical segments 102 aligned adjacent one another in a spaced configuration discussed above, a total of three gaps G will be present: a first gap G between the proximal inner surface 136 and the adjacent cylindrical segment's opposing proximal inner surface 106$p$; a second gap G between the distal outer surface 146 and the adjacent cylindrical segment's opposing distal inner surface 106$d$; and a third gap G between the most proximal cylindrical segment's opposing distal inner surface 106$d$ and the most distal cylindrical segment's opposing proximal inner surface 106$p$. The case involving three cylindrical segments 102 is illustrated in FIGS. 5 and 6 and comprises four flexibility gaps G in conformance with the foregoing discussion. Therefore, the present invention comprises an eccentric abrading head 100 having at least two flexibility gaps G. The number of flexibility gaps G in any given embodiment of the eccentric abrading head of the present invention comprises the formula "N+1", wherein N is the number of cylindrical segments 102.

The presence of the at least two flexibility gaps G confers several highly desirable performance characteristics on the eccentric abrading head 100 and rotational atherectomy device. First, the gaps G allow the drive shaft to flex freely, therefore allowing the drive shaft and abrading head 100 to be more easily inserted into and withdrawn from a patient's tortuous vasculature. This ease of insertion provides for a more atraumatic procedure.

Secondly, as described above, a differential abrasive grit size may be employed for the cylindrical segment(s) outer surface 104 vs the proximal and distal inner surfaces 106$p$, 106$d$. Thus, the outer surface's 104 abrasive may be optimized for removal of hard stenotic tissue while the proximal and distal inner surfaces 106$p$, 106$d$ may comprise an abrasive optimized for removal of soft, non-calcified and/or diffuse stenotic tissue. In the latter case, e.g., soft tissue may expand and extend a distance into flexibility gap G after compression by outer surface 104 as the abrading head 100 is moved either proximally or distally within the stenosis by the operator. The presence of abrasive optimized for soft tissue removal on the proximal and distal inner surfaces 106$p$, 106$d$ of gap G enhances the removal thereof.

Third, the flexibility gaps G provide a mechanism and a method for disrupting or breaking the hydraulic wedge that is known to result when a relatively smooth surfaced abrasive head rotates at high speed against the stenosis and/or arterial wall. The gaps G thus promote increased contact between the abrading head 100, in particular the outer surface(s) 104 and the stenosis. Thus, the inventive abrading head 100 improves abrading efficiency and efficacy.

Fourth, the flexibility gaps G allow for some flexion of the abrading head 100 during high-speed rotation. This may improve abrading efficiency and lessen trauma during the procedure. In addition, the flexibility gaps G may allow the abrading head 100 to achieve and realize a more natural, and thus more stable, oscillation frequency.

Moreover, the present inventive abrading head 100 comprises more abrasive surface area than a unitary body prior art abrading head. The abrasive surface 26 of the proximal and distal inner surfaces 106$p$, 106$d$ add a large amount of abrasive surface area not available on known unitary body devices. This added surface increases the efficiency of the rotational atherectomy procedure and reduces procedure time. As the number of eccentric abrading cylindrical segments 100 are variable, i.e., at least one cylindrical segment 100 may be used, the abrasive surface area of the inventive device 100 is customizable and may be increased or decreased as desired simply by adding or subtracting cylindrical segment(s) 100 and/or electing to not coat the inner and/or outer surfaces 106$p$, 106$d$ with abrasive.

As is well understood in the art, the abrasive material may be any suitable material, such as diamond powder, fused silica, titanium nitride, tungsten carbide, aluminum oxide, boron carbide, or other ceramic materials. Preferably the abrasive material is comprised of diamond chips (or diamond dust particles) attached directly to the tissue removing surface (s) by a suitable binder. Such attachment may be achieved using well known techniques, such as conventional electroplating or fusion technologies (see, e.g., U.S. Pat. No. 4,018, 576). Alternately the external tissue removing surface may comprise mechanically or chemically roughening the external surface(s) of the intermediate section 135, the proximal and/or distal segments 130, 140 to provide a suitable abrasive tissue removing surface. In yet another variation, the external surface may be etched or cut (e.g., with a laser) to provide small but effective abrading surfaces. Other similar techniques may also be utilized to provide a suitable tissue removing surface.

Figure 7:
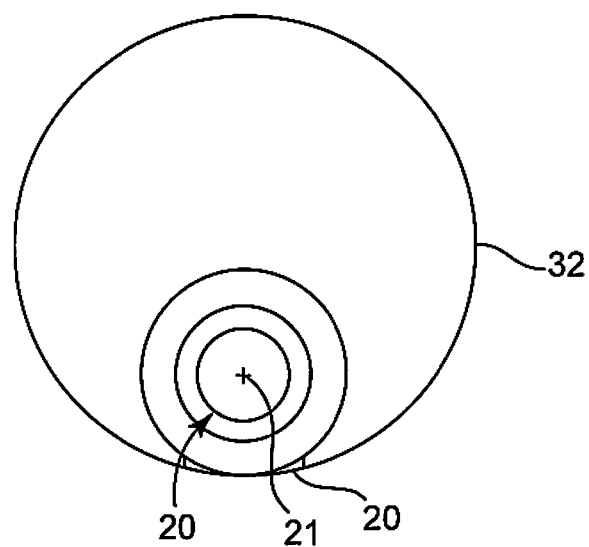
FIG. 7 is a front view of one embodiment of an eccentric cylindrical abrading segment of the present invention.

As best illustrated in FIGS. 5-7, an at least partially enclosed lumen or slot 23 may be provided longitudinally through the eccentric abrading head 100 along the rotational axis 21 of the drive shaft 20 for securing the abrading head 100 to the drive shaft 20 in a manner well known to those skilled in the art. Thus, the proximal and distal segments 130, 140 are secured to the drive shaft 20 in this manner as are the at least one cylindrical segment(s) 102 as shown in FIGS. 7 and 8A-8C. FIG. 7 illustrates one cylindrical segment 102 with a partially enclosed lumen 23 and attached to drive shaft 20. The proximal and distal segments 130, 140 similarly may comprise an at least partially enclosed lumen 23. Alternative embodiments of the proximal and distal segments 130, 140 and/or at least one cylindrical segment 100 may comprise a completely enclosed lumen 23 as, e.g., shown in the cross sectional view of FIGS. 8A-8C.

The embodiment of FIGS. 5 and 6 illustrate the proximal and distal 130, 140 segments being of symmetrical shape and length as well as equivalent slopes in the conical sections 132, 142 leading up to the intermediate section 135. Alternate embodiments may increase the length of either the proximal segment 130 or the distal segment 140, to create an asymmetrical profile. In general, the symmetry of the inventive abrading head 100 as illustrated in FIGS. 5 and 6 is preferred, though alternate embodiments may comprise a larger or smaller degree of slope in proximal and/or distal segments 130, 140. Additionally, the proximal and/or distal segments 130, 140 and/or the intermediate section 35 may have a longer or shorter length. Each such combination is within the scope of the present invention.

As described supra, in certain embodiments, the proximal and/or distal segments 130, 140 comprise conical sections 132, 140 and/or cylindrical sections 134, 144, while the intermediate section 135 is cylindrical. As is illustrated in FIGS. 7, and 8A-8C, this geometrical configuration is at least partially responsible for providing the inventive eccentric abrading head 100 with a center of mass 32 that is spaced geometrically and radially away from the longitudinal rotational axis 21 of the drive shaft 20. As illustrated in the Figures, each eccentric cylindrical segment 102 comprises a center of mass 32 that is offset from the rotational axis 21 of the drive shaft 20. In addition, the proximal and distal sections 130, 140, comprise a center of mass that is offset from the rotational axis 21 of the drive shaft 20. Offsetting the center of mass 32 from the drive shaft's axis of rotation 21 provides the eccentric abrading head 100 with an eccentricity that permits it to open an artery to a diameter substantially larger during high-speed rotation than the nominal diameter of the eccentric abrading head 100. Preferably the opened diameter is at least twice as large as the nominal resting diameter of the eccentric abrading head 100. Additionally, such offsetting of the center of mass 32 may be enhanced, manipulated and controlled by varying the amount of mass and location of mass in the intermediate section 135 by, e.g., using two or more types of materials having differing densities.

It should be understood that, as used herein, the words "eccentric" and "eccentricity" are defined and used herein to refer to either a difference in location between the geometric center of the eccentric abrading head 100 and the rotational axis 21 of the drive shaft 20, or to a difference in location between the center of mass 32 of the eccentric abrading head 100 and the rotational axis 21 of the drive shaft 20. Either such difference, at the proper rotational speeds, will enable the eccentric abrading head 100 to open a stenosis to a diameter substantially greater than the nominal diameter of the eccentric abrading head 100. Because the individual cylindrical segment(s) 102 and the proximal and distal segments 130, 140 are separated by flexibility gap G, the abrading head 100 may, during high-speed rotation, flex slightly. This flexing ability may assist in improving abrading efficiency. In addition, the eccentric abrading head 100 may, during high-speed rotation, achieve a natural oscillation frequency that is more advantageous than a solid, unitary body abrading head.

The eccentric abrading head 100 of the rotational atherectomy device of the invention may be constructed of stainless steel, tungsten and/or similar material.

Figure 8C:
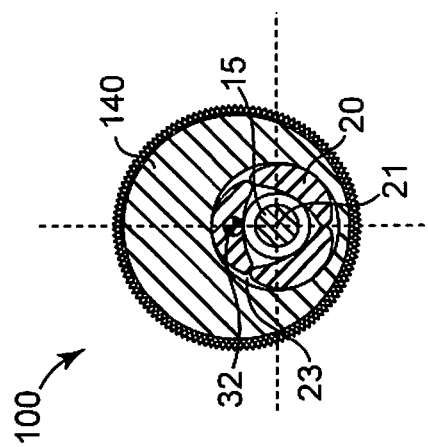
FIGS. 8A-8C are transverse cross-sectional views of one embodiment of the non-flexible eccentric cutting head of the invention.
Figure 8B:
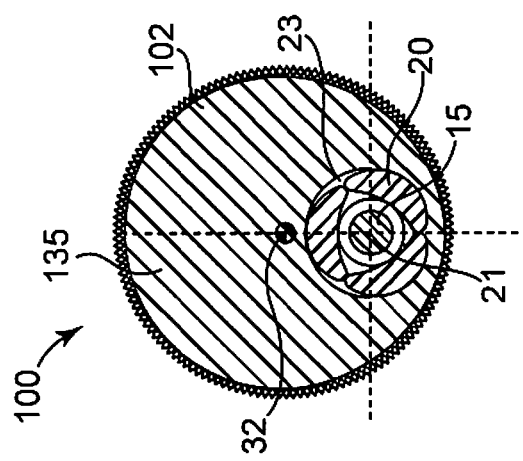
Figure 8A:
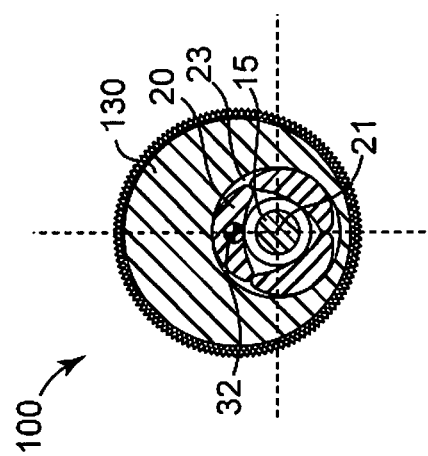

FIGS. 8A-8C depict the positions of the centers of mass 32 of three cross-sectional slices (shown as faces of transverse cross-sections) of the eccentric abrading head 100 shown in 5 and 6, with the eccentric abrading head 100 fixedly attached to the drive shaft 20 via lumen 23, the drive shaft 20 advanced over guide wire 15. As will become apparent, the proximal and/or distal segments 130, 140 and the at least one cylindrical segment 100 each comprise a center of mass 32 position relative to the rotational axis 21 of the drive shaft 20. FIG. 8B is taken at a position where the eccentric abrading head 100 has its maximum cross-sectional diameter (which, in this embodiment, is the maximum diameter of the at least one cylindrical segment 102 of the eccentric enlarged abrading head 100), and FIGS. 8A and 8C are cross-sections, respectively, of the proximal and distal segments 130, 140 of the eccentric abrading head 100. In each of these cross-sectional slices the center of mass 32 is spaced away from the rotational axis 21 of the drive shaft 20, the rotational axis of the drive shaft 20 coinciding with the center of the guide wire 15. The center of mass 32 of each cross-sectional slice also generally coincides with the geometric center of such cross-sectional slice, though as the skilled artisan will appreciate, employing materials with differing densities may allow movement of the center of mass 32 away from the geometric center. FIG. 8B illustrates the cross sectional slice of at least one cylindrical segment 102 comprising the largest cross-sectional diameter of abrading head 100, wherein both the center of mass 32 and the geometric center are located the furthest (i.e., maximally spaced away) from the rotational axis 21 of the drive shaft 20 compared with proximal and distal segments 130, 140.

Figure 9:
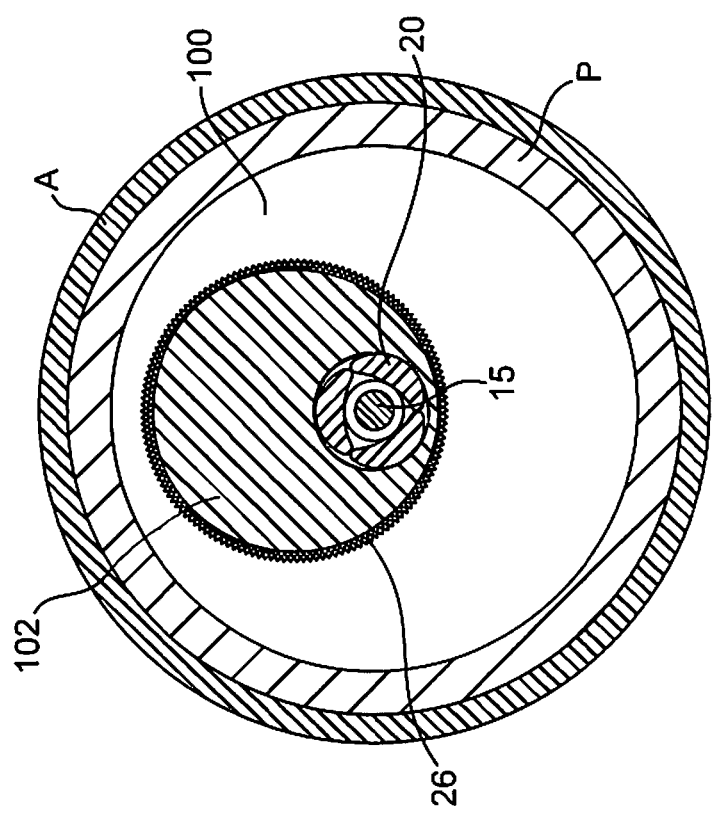
FIG. 9 is a longitudinal cross-sectional view showing the non-flexible eccentric enlarged cutting head of the invention in an at-rest (non-rotating) position after a stenosis has been substantially opened by the device.

FIG. 9 depicts the a cross-section through the at least one cylindrical segment 102 of the eccentric abrading head 100 of the present invention with guide wire 20 and the attached abrading head 100 advanced over guide wire 15 and in an "at-rest" position within the artery "A", after the stenosis has been substantially opened, thus illustrating the device's ability to open a stenosis to a diameter well in excess of the device's nominal diameter.

The extent to which a stenosis in an artery can be opened to a diameter larger than the nominal diameter of the eccentric abrading head 100 of the present invention depends on several parameters, including but not limited to, the shape of the eccentric abrading head 100, the mass of the eccentric abrading head 100, the distribution of that mass and, therefore, the location of the center of mass within the abrading head 100 with respect to the rotational axis of the drive shaft, and the speed of rotation. As should be now apparent to the skilled artisan, the mass of the abrading head 100 and the location of the center of mass may be manipulated and controlled using the present invention by adding or removing cylindrical segment(s) 102 to achieve desired amount of mass and the location of the center of the mass.

The speed of rotation is a significant factor in determining the centrifugal force with which the abrasive surface 26 of the eccentric abrading head 100 is pressed against the stenotic tissue, thereby permitting the operator to control the rate of tissue removal. Control of the rotational speed also allows, to some extent, control over the maximum diameter to which the device will open a stenosis. Applicants have also found that the ability to reliably control the force with which the abrasive surface 26 is pressed against the stenotic tissue not only permits the operator to better control the rate of tissue removal but also provides better control of the size of the particles being removed.

Figure 10:
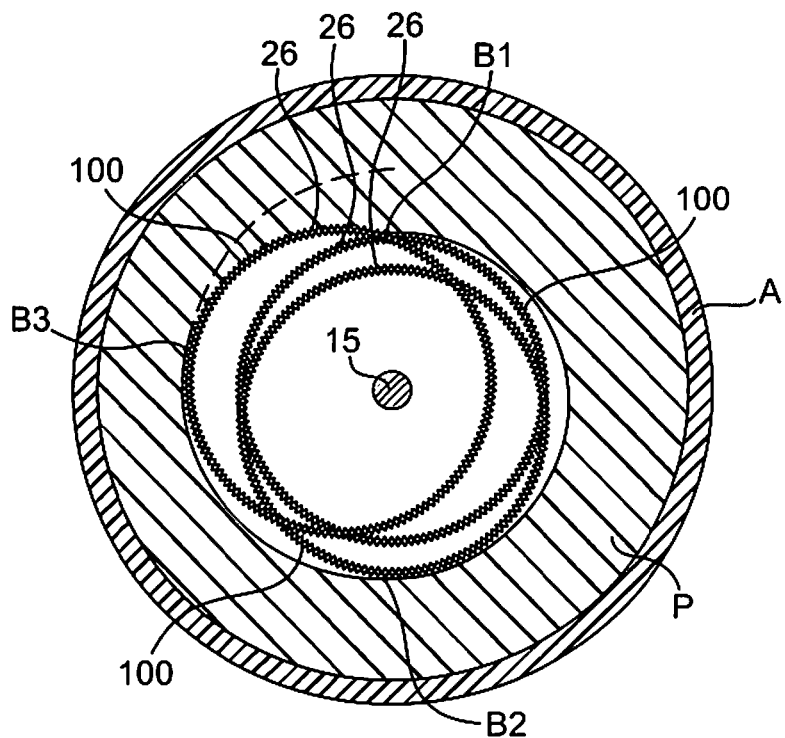
FIG. 10 is a transverse cross-sectional view illustrating three different positions of the rapidly rotating non-flexible eccentric enlarged cutting head of an eccentric rotational atherectomy device of the invention.
Figure 11:
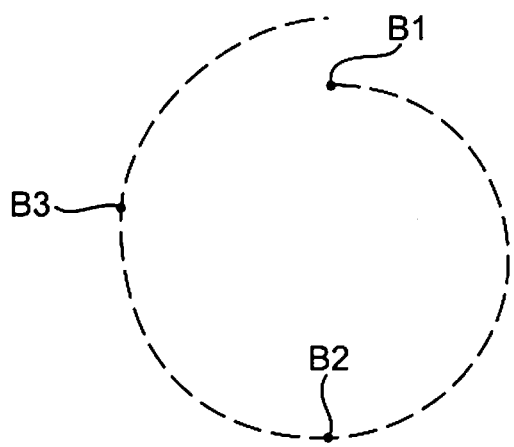
FIG. 11 is a schematic view corresponding to the three positions of the rapidly rotating non-flexible eccentric enlarged cutting head illustrated in FIG. 10.

FIGS. 10-11 illustrate the generally spiral orbital path taken by various embodiments of the eccentric abrading head 100 of the present invention, the abrading head 100 shown relative to the guide wire 15 over which the abrading head 100 has been advanced. The pitch of the spiral path is exaggerated for illustrative purposes—in reality, each spiral path of the eccentric abrading head 100 removes only a very thin layer of tissue via the abrasive 26 located on the outer surface of the cylindrical segment 102, and many, many such spiral passes are made by the eccentric abrading head 100 as the device is repeatedly moved forward and backward, i.e., translated, across the stenosis to fully open the stenosis. FIG. 10 shows schematically three different rotational positions of the eccentric abrading head 100 of a rotational atherectomy device of the invention. At each position the abrasive surface of the eccentric abrading head 100 contacts the plaque "P" to be removed—the three positions are identified by three different points of contact with the plaque "P", those points being designated in the drawing as points B1, B2, and B3. Notice that at each point it is generally the same portion of the abrasive surface of the eccentric enlarged abrading head 100 that contacts the tissue—the portion of the abrasive surface 26 on the outer surface 104 of the cylindrical segment(s) 102 that is radially most distant from the rotational axis of the drive shaft.

Although not wishing to be constrained to any particular theory of operation, applicants believe that offsetting the center of mass 32 from the axis of rotation 21 of the drive shaft 20 produces an "orbital" movement of the eccentric abrading head 100, the diameter of the "orbit" being controllable by varying, inter alia, the rotational speed of the drive shaft 20 and the number of at least one cylindrical segments 102 employed and the mass, and mass distribution, thereof. Applicants have empirically demonstrated that by varying the rotational speed of the drive shaft 20 and/or the number of cylindrical segment(s) 102, one can control the centrifugal force urging the abrasive surface 26 on the outer surface 104 of the cylindrical segment(s) 102 of the eccentric abrading head 100 against the surface of the stenosis. The centrifugal force can be determined according to the formula:

$$F_c = m\Delta x(\pi n/30)^2$$

where $F_c$ is the centrifugal force, m is the mass of the eccentric abrading head 100, $\Delta x$ is the distance between the center of mass 32 of the eccentric abrading head 100 and the rotational axis 21 of the drive shaft 20, and n is the rotational speed in revolutions per minute (rpm). Controlling this force $F_c$ provides control over the rapidity with which tissue is removed, control over the maximum diameter to which the device will open a stenosis, and improved control over the particle size of the tissue being removed.

The abrading head 100 of the present invention may comprise more mass than typical prior art high speed atherectomy abrading devices. As a result, a larger orbit, i.e., a larger rotational diameter, may be achieved during high speed rotation which, in turn, allows for use of a smaller abrading head than with prior art devices. Further, the added flexibility of the eccentric abrading head 100 allows for ease of insertion and more atraumatic procedures.

Operationally, using the rotational atherectomy device of the invention the eccentric abrading head 100 is repeatedly moved distally and proximally through the stenosis. By changing the rotational speed of the device the operator is able to control the force with which the abrasive on the outer surface 104 of the cylindrical segment(s) 102 is pressed against the stenotic tissue, thereby being able to better control the speed of the plaque removal as well as the particle size of tissue removed. In addition, by moving the abrading head 100 distally and proximally, i.e., translating the head 100, through the stenotic tissue, soft, non-calcified and/or diffuse tissue may expand to fill flexibility gaps G, thereby subjecting this tissue to the abrasive located on proximal and/or distal surfaces 106p, 106d, optimized for abrasion and removal of such tissue. Since the stenosis is being opened to a diameter larger than the nominal diameter of the eccentric abrading head 100, the cooling solution and the blood are able to constantly flow around the enlarged abrading head. In addition, the flexibility gaps G provide a channel(s) for fluid flow around the abrading head 100.

The eccentric abrading head 100 may comprise a maximum cross-sectional diameter ranging between about 1.0 mm to about 3.0 mm. Thus, the eccentric enlarged abrading head may comprise cross-sectional diameters including, but not limited to: 1.0 mm, 1.25 mm, 1.50 mm, 1.75 mm, 2.0 mm, 2.25 mm, 2.50 mm, 2.75 mm, and 3.0 mm. Those skilled in the art will readily recognize that the incremental increases of 0.25 mm within the above-listing of cross-sectional diameter are exemplary only, the present invention is not limited by the exemplary listing and, as a result, other incremental increases in cross-sectional diameter are possible and within the scope of the present invention.

Because, as described above, the eccentricity of the eccentric abrading head 100 is dependent on a number of parameters, applicants have found that the following design parameters may be considered regarding the distance between the rotational axis 21 of the drive shaft 20 and the geometric center of a face of a transverse cross-section, taken at a position of maximum cross-sectional diameter of the eccentric abrading head 100, i.e., through the at least one cylindrical segment 102: for a device having an eccentric enlarged abrading head with a maximum cross-sectional diameter between about 1.0 mm and about 1.5 mm, desirably the geometric center should be spaced away from the rotational axis of the drive shaft by a distance of at least about 0.02 mm, and preferably by a distance of at least about 0.035 mm; for a device having an eccentric enlarged abrading head with a maximum cross-sectional diameter between about 1.5 mm and about 1.75 mm, desirably the geometric center should be spaced away from the rotational axis of the drive shaft by a distance of at least about 0.05 mm, preferably by a distance of at least about 0.07 mm, and most preferably by a distance of at least about 0.09 mm; for a device having an eccentric enlarged abrading head with a maximum cross-sectional diameter between about 1.75 mm and about 2.0 mm, desirably the geometric center should be spaced away from the rotational axis of the drive shaft by a distance of at least about 0.1 mm, preferably by a distance of at least about 0.15 mm, and most preferably by a distance of at least about 0.2 mm; and for a device having an eccentric enlarged abrading head with a maximum cross-sectional diameter above 2.0 mm, desirably the geometric center should be spaced away from the rotational axis of the drive shaft by a distance of at least about 0.15 mm, preferably by a distance of at least about 0.25 mm, and most preferably by a distance of at least about 0.3 mm.

Design parameters can also be based on the location of the center of mass. For a device having an eccentric abrading head 100 with a maximum cross-sectional diameter between about 1.0 mm and about 1.5 mm, i.e., the maximum diameter of the at least one cylindrical segment 102, desirably the center of mass should be spaced away from the rotational axis of the drive shaft by a distance of at least about 0.013 mm, and preferably by a distance of at least about 0.02 mm; for a device having an eccentric abrading head 100 with a maximum cross-sectional diameter between about 1.5 mm and about 1.75 mm, desirably the center of mass should be spaced away from the rotational axis of the drive shaft by a distance of at least about 0.03 mm, and preferably by a distance of at least about 0.05 mm; for a device having an eccentric enlarged abrading head with a maximum cross-sectional diameter between about 1.75 mm and about 2.0 mm, desirably the center of mass should be spaced away from the rotational axis of the drive shaft by a distance of at least about 0.06 mm, and preferably by a distance of at least about 0.1 mm; and for a device having an eccentric enlarged abrading head with a maximum cross-sectional diameter above 2.0 mm, desirably the center of mass should be spaced away from the rotational axis of the drive shaft by a distance of at least about 0.1 mm, and preferably by a distance of at least about 0.16 mm.

Preferably the design parameters are selected so that the eccentric abrading head 100 is sufficiently eccentric that, when rotated over a stationary guide wire 15 (held sufficiently taut so as to preclude any substantial movement of the guide wire) at a rotational speed greater than about 20,000 rpm, at least a portion of the outer surface 104 of the at least one cylindrical segment 102 may rotate through a path (whether or not such path is perfectly regular or circular) having a diameter larger than the maximum nominal diameter of the eccentric abrading head 100, i.e., greater than the diameter of the at least one cylindrical segment 102. For example, and without limitation, for an eccentric abrading head 100 having a maximum diameter between about 1.5 mm and about 1.75 mm, at least a portion of the abrading head 100 may rotate through a path having a diameter at least about 10% larger than the maximum nominal diameter of the eccentric enlarged abrading head 100, preferably at least about 15% larger than the maximum nominal diameter of the eccentric abrading head 100, and most preferably at least about 20% larger than the maximum nominal diameter of the abrading head 100. For an abrading head 100 having a maximum diameter between about 1.75 mm and about 2.0 mm, at least a portion of the abrading head 100 may rotate through a path having a diameter at least about 20% larger than the maximum nominal diameter of the abrading head 100, preferably at least about 25% larger than the maximum nominal diameter of the abrading head 100, and most preferably at least about 30% larger than the maximum nominal diameter of the abrading head 100. For an eccentric abrading head 100 having a maximum diameter of at least about 2.0 mm, at least a portion of the abrading head 100 may rotate through a path having a diameter at least about 30% larger than the maximum nominal diameter of the eccentric abrading head 100, and preferably at least about 40% larger than the maximum nominal diameter of the eccentric enlarged abrading head 100.

Preferably design parameters are selected so that the enlarged abrading head 100 is sufficiently eccentric that, when rotated over a stationary guide wire 15 at a speed between about 20,000 rpm and about 200,000 rpm, at least a portion of its abrading head 100 rotates through a path (whether or not such path is perfectly regular or circular) with a maximum diameter that is substantially larger than the maximum nominal diameter of the resting abrading head 102, i.e., substantially larger than the diameter of the resting at least one cylindrical segment 102. In various embodiments, the present invention is capable of defining a substantially orbital path with a maximum diameter that is incrementally between at least about 50% and about 400% larger than the maximum nominal diameter of the resting abrading head 102. Desirably such orbital path comprises a maximum diameter that is between at least about 200% and about 400% larger than the maximum nominal diameter of the resting eccentric enlarged abrading head 100, i.e., substantially larger than the diameter of the resting at least one cylindrical segment 102.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A high-speed rotational atherectomy device for opening a stenosis in an artery having a given diameter, comprising:
    a guide wire having a maximum diameter less than the diameter of the artery;
    a flexible elongated, rotatable drive shaft advanceable over the guide wire, the drive shaft having a rotational axis;
    an eccentric proximal segment defining a drive shaft lumen therethrough, wherein the proximal segment is mounted on the drive shaft;
    at least one eccentric cylindrical segment separate from the eccentric proximal segment, the at least one eccentric cylindrical segment defining a drive shaft lumen therethrough, wherein the at least one eccentric cylindrical segment is mounted distally and separately from the proximal segment on the drive shaft, wherein the at least one eccentric cylindrical segment and the proximal segment are spaced apart along the drive shaft by a first flexibility gap;
    an eccentric distal segment separate from the at least one eccentric cylindrical segment, the distal segment defining a drive shaft lumen therethrough, wherein the distal segment is mounted distally and separately from the at least one eccentric cylindrical segment on the drive shaft, wherein the at least one eccentric cylindrical segment and the distal segment are spaced apart along the drive shaft by a second flexibility gap.

2. The rotational atherectomy device of claim 1, wherein the proximal segment comprises a proximal conical section.

3. The rotational atherectomy device of claim 2, wherein the proximal segment further comprises a proximal cylindrical section.

4. The rotational atherectomy device of claim 2, wherein the distal segment comprises a distal conical section.

5. The rotational atherectomy device of claim 4, wherein the distal segment comprises a distal conical section and a distal cylindrical section.

6. The rotational atherectomy device of claim 1, wherein the at least one eccentric cylindrical segment comprises at least one eccentric abrading cylindrical segment.

7. The rotational atherectomy device of claim 6, further comprising two or more eccentric abrading cylindrical segments, wherein each of the two or more eccentric abrading cylindrical segments are adjacent to at least one eccentric abrading cylindrical segment and in spaced proximity with the at least one adjacent eccentric abrading cylindrical segment.

8. The rotational atherectomy device of claim 6, wherein the total number of flexibility gaps comprises the number of eccentric abrading cylindrical segments plus one.

9. The rotational atherectomy device of claim 6, wherein the at least one eccentric abrading cylindrical segment comprises an outer surface and a proximal inner surface and a distal inner surface, the outer surface, proximal inner surface and distal inner surface comprising abrasive surfaces.

10. The rotational atherectomy device of claim 9, wherein the outer surface comprises abrasive that is optimized for calcified stenotic tissue and wherein the proximal inner surface and distal inner surface comprise abrasive that is optimized for soft, non-calcified stenotic tissue.

11. The rotational atherectomy device of claim 1, wherein the proximal segment and distal segment each comprise a center of mass that is offset from the rotational axis of the drive shaft.

12. The rotational atherectomy device of claim 6, wherein the at least one eccentric cylindrical segment comprises a center of mass that is spaced radially away from the rotational axis of the drive shaft.

13. The rotational atherectomy device of claim 12, wherein the center of mass of the eccentric proximal segment, distal segment and at least one eccentric abrading cylindrical segment comprises an offset from the rotational axis of the drive shaft that may be controlled by adding or removing one or more of the at least one eccentric abrading cylindrical segments.

14. The rotational atherectomy device of claim 1, wherein the at least two flexibility gaps allow for flexion between the at least one eccentric abrading cylindrical segment, the proximal segment and the distal segment.

* * * * *